US00PP10071P

United States Patent [19]

Carruth

[11] Patent Number: Plant 10,071

[45] Date of Patent: Oct. 21, 1997

[54] HYBRID TEA ROSE PLANT VARIETY NAMED 'WEKJUVOO'

[75] Inventor: Thomas F. Carruth, Altadena, Calif.

[73] Assignee: Weeks Wholesale Rose Grower, Inc., Upland, Calif.

[21] Appl. No.: 656,454

[22] Filed: May 31, 1996

[51] Int. Cl.[6] ..... A01H 5/00

[52] U.S. Cl. ..... Plt./11

[58] Field of Search ..... Plt./11, 12, 13, Plt./1

[56] References Cited

U.S. PATENT DOCUMENTS

P.P. 7,944 8/1992 Warriner ..... Plt./11

P.P. 8,248 6/1993 Meilland ..... Plt./11

*Primary Examiner*—Howard J. Locker

*Attorney, Agent, or Firm*—Christie, Parker & Hale, LLP

[57] ABSTRACT

A new variety of Hybrid Tea rose suitable for garden decoration, having flowers of bright orange-yellow coloration blushed red.

1 Drawing Sheet

BACKGROUND OF THE INVENTION

This invention relates to a new and distinct variety of Hybrid Tea rose. The varietal denomination of the new variety is 'Wekjuvoo'. The new variety is bushy and upright and suitable for outdoor garden decoration. It has as its seed parent the variety known as 'Aromiclea' (U.S. Plant Pat. No. 6,121) and an undisseminated seedling of my creation as its pollen parent.

SUMMARY OF THE INVENTION

Among the features which distinguish the new variety from other presently available and known commercial rose cultivars are the following combination of characteristics: its dark stem color, its brightly colored large flowers borne on a compact plant and its very dark red new foliage. 'Wekjuvoo' may be asexually propagated by cuttings, budding, or grafting.

Asexual reproduction of the new variety by budding as performed in Kern County and Upland, Calif., shows that the foregoing and other distinguishing characteristics come true to form and are established and transmitted through succeeding propagations.

Comparison with Parents

The new rose may be distinguished from its seed parent, 'Aronmiclea' by the following combination of characteristics: whereas 'Wekjuvoo' produces a medium height plant, 'Aromiclea' produces a significantly taller plant. The seed parent has numerous prickles of varying sizes, whereas the new variety has significantly fewer prickles with less variation in sizes. 'Aromiclea' has medium small foliage with a very glossy finish, whereas 'Wekjuvoo' has larger foliage with a matte finish.

The new variety may be distinguished from its pollen parent, an undistributed seedling, by the following combination of characteristics: whereas 'Wekjuvoo' bears large flowers of orange, yellow and scarlet combination, the pollen parent bears smaller flowers of a pure yellow coloration. The pollen parent is a Floribunda, bearing its flowers mostly in clusters; whereas the new variety is a Hybrid Tea, bearing its flowers mostly one per stem.

BRIEF DESCRIPTION OF ILLUSTRATION

The accompanying photograph illustrates specimens of the new variety and shows the flowering thereof from bud to full bloom depicted in color as nearly correct as it is possible to make in a color illustration of the character. Throughout this specification, color values are based upon The Colour Chart of The Royal Horticultural Society of London, England, except where common terms of color definition are employed.

DESCRIPTION OF THE NEW VARIETY

The following description is of specimens of the new cultivar grown outdoors in Upland, Calif. in the month of October. Phenotypic expression may vary with environmental, cultural and climatic conditions, as well as differences in conditions of light and soil.

Flower

The new variety bears its flowers usually singly, sometimes in clusters of two to three per stem. Flowers are borne in irregular, rounded clusters on strong short-to-medium stems (about 32 to about 44 cm.) for the class. Outdoors the plant blooms abundantly and nearly continuously during the growing season. The flowers have a slight fruity fragrance.

Bud

The peduncle is of average-to-long length for the class (about 8 to about 12 cm.), of heavy caliper and usually erect. It is almost entirely smooth with no stipitate glands and few hairs. Peduncle color is between 144A and 138B usually moderately blushed on the side facing the sun with between 166A and 183A.

Before the calyx breaks, the bud is of medium to large size for the class (about 1.7 to about 2.2 cm. in diameter at the widest point), medium in length (about 2.5 to about 3.0 cm.), and pointed to ovoid in shape. The surface of the bud bears very few stipitate glands and some hairs, usually with slender foliaceous parts extending beyond the tip of the bud equal to ½ or more of its length. Bud color is between 144A and 138A sometimes lightly blushed on the side facing the sun with between 166A and 183A.

The inner surface of the sepals is covered with fine wooly tomentum; sepal margins are lined with few stipitate glands and numerous hairs.

As the petals open the bud is medium to large for the class about 2.5 to about 3.0 cm. in diameter at the widest point), nedium to long in length (about 3.8 to about 4.3 cm.), and noderately pointed to ovoid in form. The color of the under surfaces of the newly opened petals is between 24B and 16A with a moderately large zone at the point where the petal attaches of near 9C. Areas exposed to the sun often blush to as deep as between 46B and 47B. The color of the upper surfaces of the newly opened petals is between 24A and 17D with a medium sized zone at the point where the petal attaches of near 14B. The bud opens up well and is generally not prevented from opening by wet, cold, hot or dry weather.

Bloom

When fully open, the bloom is medium to large for the class, ranging from about 10.5 to about 13 cm. in diameter. Petalage is double with about 34 to 38 petals and about 2 to 7 petaloids arranged regularly. When partially open, the bloom form is moderately high centered, and the petals are somewhat tightly spiraled with petal edges moderately rolled outward.

When fully open, the bloom form is more flat to cupped, and the petals are more loosely cupped to undulated with petal edges more rolled to quilled outward.

Petals

The substance of the petals is very heavy and of medium to thick thickness, with upper surfaces somewhat satiny and under surfaces slightly shiny. The outer petals are nearly round to very broadly obovate in shape with rounded apices.

Newly Opened Flower

The under surface of the outer, intermediate and inner petals is between 24B and 16B with a moderately large zone at the point where the petal attaches of near 9C.

The upper surface of the outer petals is between 23C and 17D with a medium sized zone at the point where the petal attaches of between 14B and 13A. Areas exposed to the sun lightly blush with between 46C and 47B. The upper surface of the intermediate and inner petals is of similar coloration with less evidence of a blush color.

The general tonality of the newly opened flower is between 23C and 17D with the outermost petals lightly blushed with between 46C and 47B.

Three Day Old Flower

The under surface of the outer and inner petals is between 20B and 16D with a large zone at the point of attachment of near 10B.

The upper surface of the outer and inner petals is between 21D and 16D with a medium sized zone at the point of attachment of near 12A. Areas exposed to the sun blush to as deep as between 45D and 42C.

On the spent bloom, the petals usually drop off cleanly.

In Upland, Calif., in October, blooms on the bush growing outdoors generally last from four to five or more days. Cut roses grown outdoors and kept at normal indoor living temperatures generally last from five or more days.

Male Reproductive Organs

Stamens are average in number and are arranged regularly about the pistils. The filaments are of irregular lenghts, most with anthers. The anthers are somewhat small for the class and all open approximately at the same time. Anther color is near 17A when immature and near 166C at maturity. Pollen is moderate to abundant and near 21C in color.

Female Reproductive Organs

Pistils vary in number (approximately 45). The styles are mostly even, moderately long in length, somewhat thin to average in caliper, and moderately bunched to columnar. Stigma and style color is near 9C. Ovaries are usually all enclosed in the calyx. Hips are of average length (about 3.0 to 3.5 cm.), very globular in form, and near 33A in color when ripe. The hip surface is very smooth with very thick fleshy walls. Seeds are average to many in number (approximately 16 to 19), and usually medium in size.

Foliage

The compound leaves are usually comprised of three to five or more leaflets and are borne in normal quantities. The leaves are medium to large for the class (about 12.5 to about 10 cm. in length and about 8 to about 9.5 cm. in width at the widest point), moderately heavy to leathery in texture, and matte in finish. The leaflets are medium to large for the class (about 4.5 to about 6.5 cm. in length and about 2.7 to about 3.8 cm. in width at the widest point), broadly oval in shape with somewhat acute apices and rounded to acute bases. Their margins are doubly serrate to irregular.

The upper surface of the mature leaf is between 137A and 139A, sometimes lightly washed with between 183A and 187A. The under surface of the mature leaf is between 138B and191A. The upper surface of the young leaf is darker than between 187A and 183A. The under surface of the young leaf is between 183A and 187A.

The rachis is somewhat heavy in caliper. The upper side of the rachis is deeply grooved and moderately smooth with few stipitate glands and hairs on the edges. The under side of the rachis is also moderately smooth with few stipitate glands. Often the rachis color is washed heavily with between 183A and 187A.

The stipules are medium to long in length with medium width medium length straight points that usually turn out at an angle of more than 45 degrees.

The plant displays an above average degree of resistance to powdery mildew and rust as compared to other commercial varieties grown under comparable conditions in Upland, Calif.

Growth

The plant has a bushy upright medium height habit (about 120 to 155 cm. in height and about 90 to about 110 cm. spread at the widest point), with full branching. It displays vigorous growth and the canes are medium caliper for the class.

The color of the major stems is near 146C. They bear several large prickles and few small prickles which are of medium length for the class (about 0.6 to 0.8 cm). The prickles are slightly hooked and angled moderately downward with a somewhat long moderately narrow base; prickle color is near 166B.

The color of the branches is between 144A and 139B, moderately suffused, especially on the side facing the sun, with as dark as between 175A and 183A. They bear several large prickles and some small prickles which are of similar shape and size to those on the major stem; prickle color is between 175A and 183A.

The color of the new shoots is between 144A and 144B heavily suffused, especially on the side facing the sun, with as dark as between 187A and 183A. They bear several large prickles and some small prickles which are of similar shape and size to those on the major stems; prickle color is between 183A and 187A.

I claim:

1. A new and distinct variety of Hybrid Tea rose plant substantially as herein described and illustrated.

* * * * *

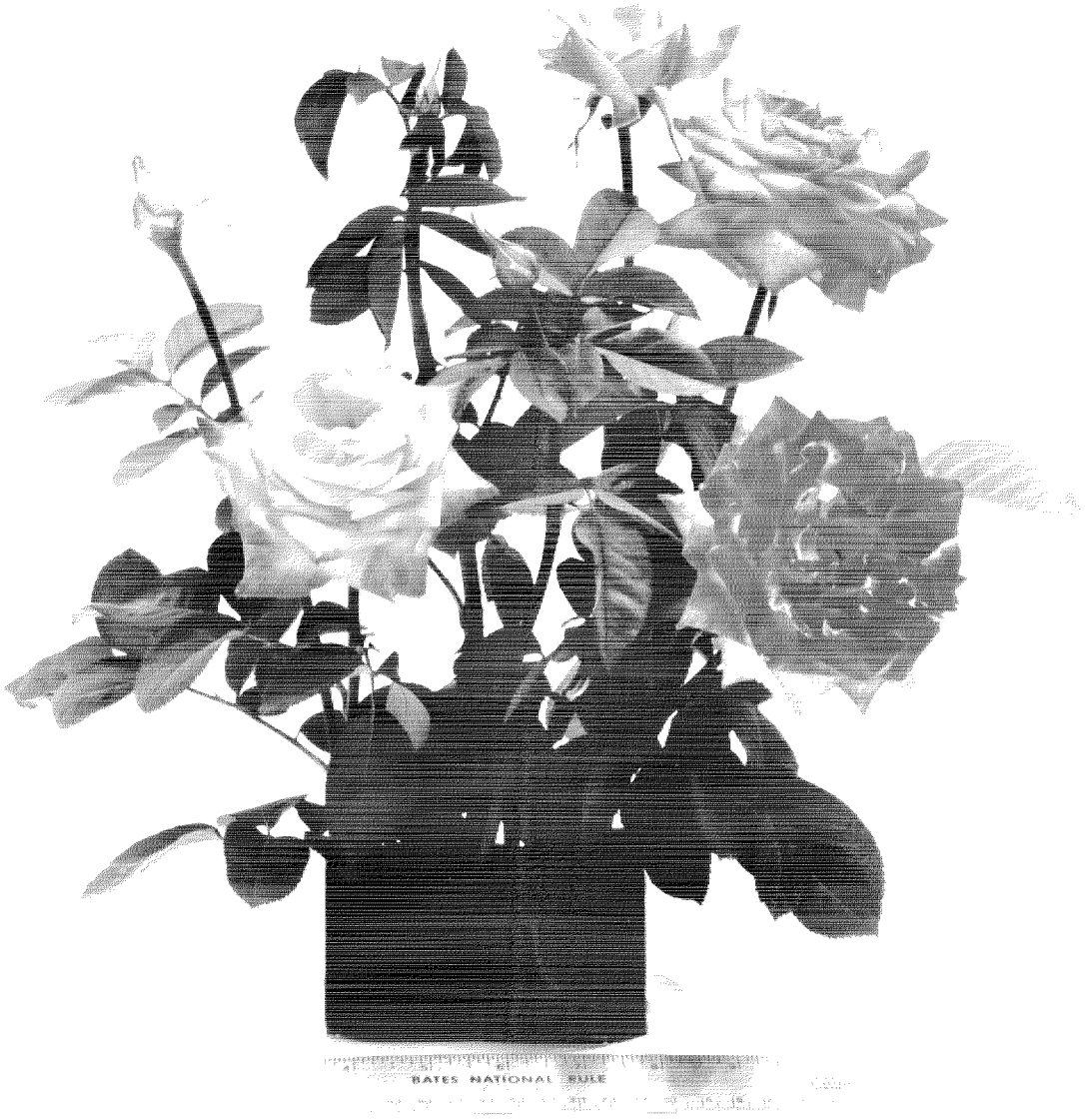
BATES NATIONAL RULE

UNITED STATES PATENT AND TRADEMARK OFFICE

CERTIFICATE OF CORRECTION

PATENT NO. : Plant 10,071
DATED : October 21, 1997
INVENTOR(S) : Thomas F. Carruth It is certified that error appears in the above-indentified patent and that said Letters Patent is hereby corrected as shown below:

Column 1, line 32, change 'Aronmiclea' to -- 'Aromiclea' --.
Column 3, line 32, after "apices." insert -- The inner petals are broadly ovovate in shape with rounded apices. --.
Column 3, line 57, between the paragraph ending with "45D and 42C." and the paragraph beginning with "On the spent bloom," insert the following paragraph:
-- The general tonality of the three day old flower is between 45D and 42C. --.
Column 4, line 4, change "lenghts" to -- lengths --.

Signed and Sealed this

Second Day of February, 1999

*Attest:*

*Acting Commissioner of Patents and Trademarks*

*Attesting Officer*